United States Patent [19]
Williamson et al.

[11] Patent Number: 5,405,344
[45] Date of Patent: Apr. 11, 1995

[54] ARTICULABLE SOCKET JOINT ASSEMBLY FOR AN ENDOSCOPIC INSTRUMENT FOR SURGICAL FASTNER TRACK THEREFOR

[75] Inventors: Warren P. Williamson, Loveland; Steven Burnett, W. Chester; Jack E. Smith, Dayton; Mark Fogelberg, Loveland; E. David Allen, Okeana, all of Ohio

[73] Assignee: Ethicon, Inc., Somerville, N.J.

[21] Appl. No.: 130,068

[22] Filed: Sep. 30, 1993

[51] Int. Cl.$^6$ .............................................. A61B 17/00
[52] U.S. Cl. ....................................... 606/1; 606/205; 606/143; 604/95
[58] Field of Search .................. 606/1, 205, 208, 174, 606/193; 604/95; 128/20; 607/154

[56] References Cited

U.S. PATENT DOCUMENTS

| | | | |
|---|---|---|---|
| 3,674,014 | 7/1972 | Tillander | 604/95 |
| 4,000,743 | 1/1977 | Weaver | 604/95 X |
| 4,672,964 | 6/1987 | Dee | 606/170 |
| 4,921,482 | 5/1990 | Hammerslag et al. | 604/95 |
| 5,152,748 | 10/1992 | Chastagner | 604/95 |
| 5,209,747 | 5/1993 | Knoepfler | 606/208 X |
| 5,237,985 | 8/1993 | Hodgson et al. | 128/20 X |
| 5,271,543 | 12/1993 | Grant et al. | |
| 5,275,608 | 1/1994 | Forman et al. | |
| 5,289,963 | 3/1994 | McGarry et al. | |
| 5,314,466 | 5/1994 | Stern et al. | 607/159 |

Primary Examiner—Peter A. Aschenbrenner
Attorney, Agent, or Firm—Paul A. Coletti

[57] ABSTRACT

An articulable assembly is provided for an endoscopic instrument along with a surgical fastener track therefor. The assembly includes a distal end portion for supporting an end effector to effect tissue manipulation while carrying out a surgical procedure within a body cavity. The assembly includes an articulable joint connecting an elongate support housing with the distal end portion. The joint includes a hollow socket and a convex member that is received in the socket. The convex member defines a passageway for accommodating an actuator extending from the housing through the joint to actuate the end effector. An operator is provided on the housing and extends to the socket or convex member for moving the distal end portion into and out of alignment with the housing. A flexible track is provided for guiding fasteners through the joint.

11 Claims, 9 Drawing Sheets

ARTICULABLE SOCKET JOINT ASSEMBLY FOR AN ENDOSCOPIC INSTRUMENT FOR SURGICAL FASTNER TRACK THEREFOR

TECHNICAL FIELD

This invention relates generally to surgical instruments used in endoscopic procedures.

BACKGROUND OF THE INVENTION AND TECHNICAL PROBLEMS POSED BY THE PRIOR ART

Endoscopic surgical techniques have become widely accepted. As used herein, the term "endoscopic" pertains generally to the use of a surgical instrument which is inserted into a body cavity in conjunction with an endoscope which is inserted into the same body cavity. The endoscope permits visual inspection, with or without magnification, of the interior of the body cavity and permits observation of the operation of the surgical instrument for therapeutic or diagnostic purposes.

In a typical endoscopic surgical procedure, the abdominal cavity of a human or animal subject is insufflated with a sterile gas, such as carbon dioxide, in order to provide increased maneuvering room within the body cavity for endoscopic instruments. Then, conventional trocars are inserted into the subject's body cavity through the surrounding skin, tissue, and musculature. A conventional trocar typically consists of a trocar cannula which houses an elongated trocar obturator. Trocar obturators typically have a piercing point, although other types of obturators are also available.

After each trocar has been positioned within the body cavity adjacent the target surgical site, the trocar obturator is removed leaving the trocar cannula as a pathway to the body cavity. A plurality of trocar cannulas are typically placed in this manner. The surgeon can then insert an endoscope through one of the trocar cannulas and can insert various types of endoscopic, surgical instruments through one or more of the other trocar cannulas at the target surgical site where the diagnostic or therapeutic surgical procedure is performed.

The endoscope is typically connected to a video camera, and the output from the video camera is fed to a video monitor which displays the surgical site and the end of the endoscopic instrument at the surgical site. Examples of endoscopic instruments include ligating clip appliers, tissue cutters, electrosurgical instruments, tissue graspers, needle graspers, cannulas, tissue manipulators, and the like.

Although endoscopic surgical procedures offer many advantages, there are some problems associated with these procedures as conventionally practiced. For example, because the surgeon typically views the display on the video monitor as he manipulates instruments within the body cavity, the video display provides the surgeon with only a two-dimensional view of the surgical site, and there is a consequent loss of depth perception.

Another problem relates to engaging tissue from the instrument insertion direction. Many conventional, endoscopic instruments, such as graspers and scissors include a distal end mechanism for engaging the tissue in a way that effects the desired result (e.g., squeezing or cutting the tissue). Such distal end mechanisms can be generally described as "end effectors." In many conventional, endoscopic instruments, the end effector is mounted to, and extends generally linearly with, a rigid, straight shaft of the instrument.

Depending upon the nature of the operation to be performed on the tissue within the body cavity, it may be desirable to provide an end effector which can be angled or articulated relative to the longitudinal axis of the instrument shaft. This can permit the surgeon to more easily engage the tissue in some situations.

A further problem relates to the potential for blocking part of the field of view with the endoscopic instrument. Thus, the use of an endoscopic instrument with an articulating distal end would permit the surgeon to engage the tissue with the distal end of the end effector laterally offset relative to the instrument's main shaft. This would permit the engaged tissue and distal end of the end effector to be better viewed through an adjacent endoscope with little or not interference from the main shaft.

Although a number of designs have been proposed for articulating endoscopic instruments, and although articulating endoscopes and other instruments are commercially available, it would be desirable to provide an improved design for accommodating articulation of an end effector.

In particular, it would be advantageous to provide an articulating instrument with the capability for orienting the end effector at a substantial oblique angle relative to the longitudinal axis of the instrument. Further, it would be beneficial if such an improved design permitted articulation in any radial direction around the longitudinal axis of the instrument.

In endoscopic surgery it may be desirable in some situations to sense environmental characteristics at the surgical site (e.g., temperature, chemical, etc.). Further, it may be desirable to sense the actual presence or position of a component of the instrument. In addition, it may be beneficial to provide conduits for irrigation or aspiration at the surgical site. It may also be necessary to provide clips or staples at the site and to provide means, as part of the end effector, for applying the clips or staples. Accordingly, it would be especially advantageous to provide an improved articulable assembly which can accommodate internal sensor lines, aspiration conduits, irrigation conduits, flexible actuator members, as well as the feeding and application of fasteners (e.g., of clips and staples). Such an improved articulable assembly should preferably have sufficient interior space to accommodate internal passages and components and to permit the movement of such components through the articulable assembly.

It would also be advantageous if such an improved articulable assembly for an endoscopic instrument could be provided with a relatively smooth exterior configuration having a minimum of indentations and projections that might serve as sites for contaminants and be hard to clean or that might be more likely to catch on, or tear, adjacent tissue.

It would also be beneficial if such an improved articulable assembly could be provided with sufficient strength to accommodate relatively high moments and forces during operation of the instrument end effector in an articulated orientation as well as in a straight orientation.

An improved articulable assembly should desirably also permit relatively precise control of the orientation of the end effector relative to the longitudinal axis of the instrument. Further, it would be beneficial if such control could be exercised with a minimal amount of required input force or torque. Additionally, such an improved articulable assembly should easily accommodate operation and control from the proximal end of the instrument exterior of the body cavity.

Also, it would be desirable to provide a system for transporting fasteners, such as ligating clips or staples, through the articulable assembly. Such a system should accommodate movement of the fasteners when the end effector is articulated, as well as when the end effector is aligned with the instrument main shaft. Further, such a fastener transport system should desirably isolate the fasteners within the assembly from adjacent mechanisms so as to avoid interference with the fasteners and/or contamination thereof.

The present invention provides an improved articulable assembly for an instrument used in an endoscopic procedure which can accommodate designs having the above-discussed benefits and features.

SUMMARY OF THE INVENTION

According to the principles of the present invention, a unique, articulable assembly is provided for an endoscopic instrument and permits articulation of the instrument end effector in a controlled manner. The assembly includes a joint which is relatively strong and can withstand the moments and forces to which it is subjected during articulation as well as during operation of the end effector.

The assembly is readily operated from the proximal end of the instrument without requiring the application of an excessively high input forces or torques.

The assembly provides a significant amount of internal clearance to accommodate components extending from the proximal end of the instrument to the end effector. The internal region of the assembly can also accommodate the passage of fasteners, such as ligating clips or staples.

The assembly can be provided with a relatively smooth exterior configuration to minimize potential contamination sites or tissue snagging sites.

The assembly includes a distal end portion for supporting an end effector to effect tissue manipulation while carrying out a surgical procedure within a body cavity.

An articulable joint connects the distal end portion to an elongate support housing. The joint includes a hollow socket and a convex member that is received in the socket. The convex member defines a passageway for accommodating an actuator extending from the housing through the joint to actuate the end effector.

An operator is provided on the housing and extends to either the socket or the convex member for moving the distal end portion into and out of alignment with the housing.

According to another aspect of the invention, a track is provided for guiding at least one surgical fastener through an articulable joint in an instrument for use in an endoscopic procedure.

The track includes a tube of material which is sufficiently flexible to accommodate bending through the joint. The tube defines a longitudinal passage with a transverse cross-sectional configuration for accommodating and maintaining the fastener generally in a predetermined orientation while the fastener moves along the passage.

The tube passage is at least in part defined by two generally opposed wall portions. The wall portions each define a longitudinal groove that is open toward the other wall portion. The size of the groove opening can vary in response to compressive and tensile bending loads.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

One aspect of the present invention relates to a unique, articulable assembly which can be employed in an endoscopic instrument to accommodate articulation of an end effector with relatively little required force or torque applied at the proximal end of the instrument. The articulable assembly has a substantial amount of internal clearance to accommodate end effector actuating members, sensor lines, clips or staples, irrigation conduits, aspirator conduits, and the like. The articulable assembly is relatively strong and can be provided with an exterior configuration that minimizes structural projections that might snag on tissue or accumulate contaminants.

In addition, the articulable assembly can be employed with instruments for effecting a variety of functions with respect to the surgical site, and these functions can include, but are not limited to, dissecting, cutting, grasping, clamping, applying staples or ligating clips, applying ultrasonic energy, conducting electrocautery procedures, irrigating the surgical site, or removing material from the site by aspiration or suction.

Components for various sensor systems can be routed through the novel articulable joint assembly. Such sensor systems can include, but are not limited to, systems for measuring tissue thickness or compression, tumor sensing, pulse oximitry, and dopplar effect sensing of fluid in vessels. Also, light guides and other fiber optic system components may be routed through the assembly.

Further, the articulable assembly of the present invention accommodates various designs for venting or sealing the instrument and accommodates the use of filters for filtering gas and smoke.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the instruments incorporating this invention are described in various operating positions, and terms such as upper, lower, horizontal, etc., are used with reference to these positions. It will be understood, however, that instruments incorporating this invention may be manufactured, stored, transported, used, and sold in an orientation other than the position described.

Figures illustrating the instruments show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The instruments incorporating the present invention can be used with certain conventional components the details of which, although not fully illustrated or described, will be apparent to those having skill in the art and an understanding of the necessary functions of such components.

Figures 1, 2, 3:
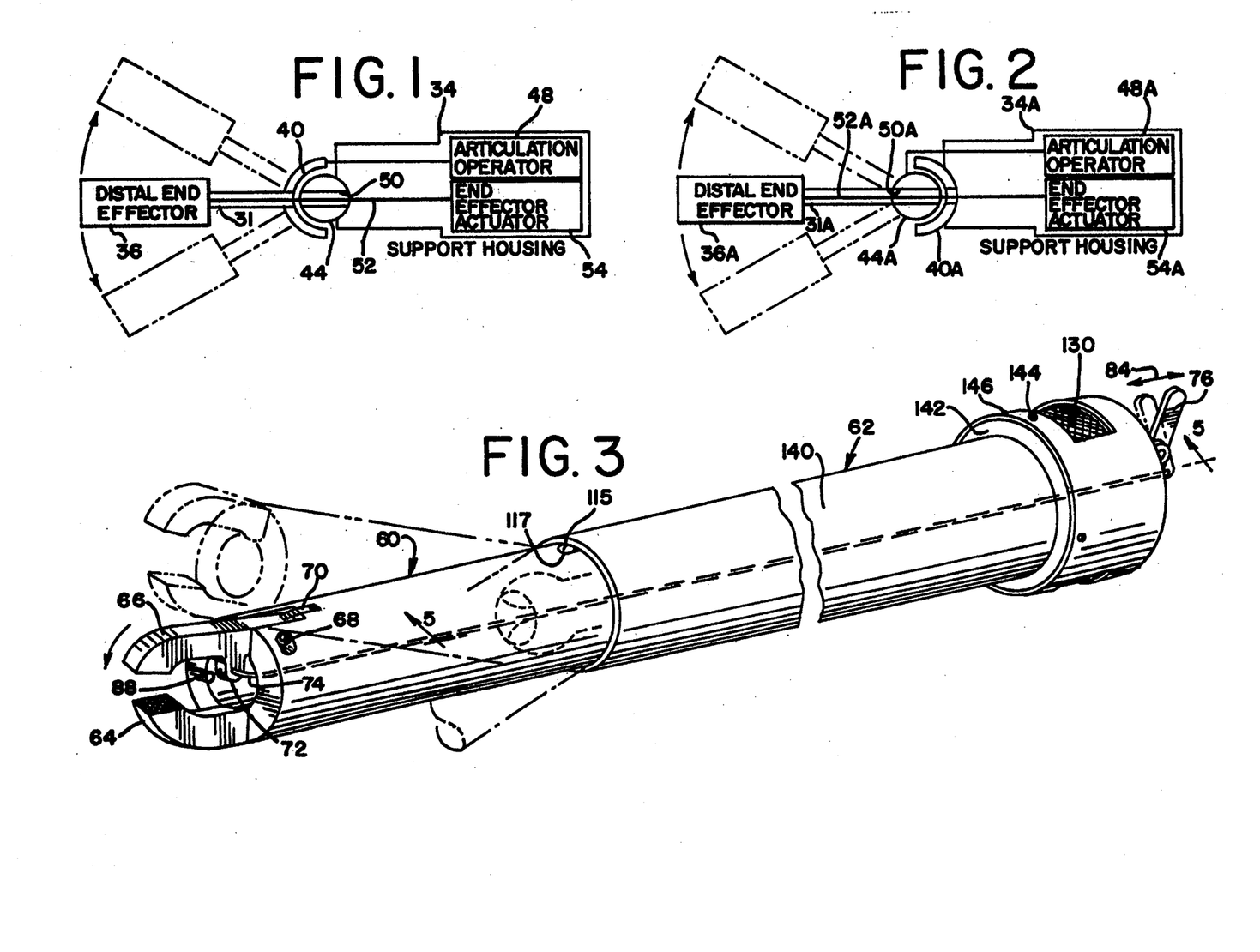
FIG. 1 is a schematic representation of an instrument incorporating a general form of an articulable assembly of the present invention.
FIG. 2 is a view similar to FIG. 1, but showing an modified form of the articulable assembly.
FIG. 3 is a simplified, perspective view of an instrument that incorporates a first embodiment of the articulable assembly of the present invention.

FIGS. 1 and 2 schematically illustrate some basic features of the articulable assembly of the present invention. The instruments illustrated in FIGS. 1 and 2 each include a proximal portion in the form of a support housing 34 (FIG. 1) or 34A (FIG. 2). This part of the instrument is grasped by the surgeon and remains outside of the patient while the rest of the instrument is inserted through the trocar cannula and into the body cavity. The instrument includes a distal end portion 31 (FIG. 1) or 31A (FIG. 2) that includes an end effector 36 (FIG. 1) or 36A (FIG. 2) which is positioned at the surgical site and actuated to manipulate the tissue in a desired manner.

Various types of end effectors for endoscopic instruments are disclosed in the catalog entitled "HOSPITAL PRICE LIST—ETHICON AND YOU. THE ULTIMATE SURGICAL TEAM—ETHICON ENDO-SURGERY—a Johnson & Johnson company EFFECTIVE FEB. 24, 1992" and distributed by Ethicon, Inc. 4545 Creek Road, Cincinnati, Ohio 45242 U.S.A. For example, see the end effectors on the following instruments shown in the catalog: the micro scissors DMS11 as shown on page 5, the straight grasper DSG20 as shown on page 5, the straight dissector DSD31 as shown on page 13, the extractor DEX40 as shown on page 13, the clamp BC10 as shown on page 13, the clip applier ER320 as shown on page 21, the linear cutter ELC60 shown on page 28, and the stapler ES100 shown on page 29. The design and operation of such end effectors are well known. Some types of end effectors are disclosed in detail in U.S. and foreign patents. See, for example, the clip applier shown in the Ethicon, Inc. U.S. Pat. No. 5,163,945.

In general, end effectors for performing the functions of the above-listed types of end effectors can, with appropriate designs, be incorporated in the articulable assemblies schematically illustrated in FIGS. I and 2. The design and operation of particular end effectors form no part of the present invention.

In FIG. 1, the distal end portion 31 is connected to the support housing 34 through an articulable joint. The joint includes a hollow socket 40 and a convex member 44 which is received in the socket 40. In particular, the socket 40 is rigidly incorporated in the distal end portion 31 while the convex member 44 is rigidly incorporated in the support housing 34.

The socket 40 can be rotated on the convex member 44 by means of an articulation operator 48 on the support housing 34. This effects articulation of the distal end effector 36. The detailed structure and operation of particular articulation operators are described in detail hereinafter.

The convex member 44 defines a passageway 50 for accommodating an actuator member 52 which extends from an end effector actuator 54 on the support housing 34 through the joint to actuate the distal end effector 36. The actuator member 52 may be characterized as part of, and an extension of, the end effector actuator 54. Such an actuator member 52 may be a flexible band for pushing a distal end effector mechanism (e.g., a link to pivot a scissors-type blade). The actuator member 52 may also be an electric cable in an electric circuit for operating an electrically powered end effector. The actuator member could also include tension cords or cables for pulling distal end effector mechanisms to effect actuation thereof. The actuator member 52 may also be a pneumatic or hydraulic line for pressurizing a suitable operator for actuating the distal end effector. The detailed design and operation of the particular end effector and actuator therefor form no part of the present invention.

The passageway 50 defined in, and through, the convex member 44 is preferably sufficiently large to accommodate one or more end effector actuator members 52 as well as additional components such as irrigation conduits, aspiration conduits, and sensor lines (electrical, pneumatic, etc.).

In the other form of the instrument illustrated in FIG. 2, a convex member 44A is rigidly incorporated in the distal end portion 31A. The convex member 44A defines a passageway 50A and is received in a socket 40A which is rigidly incorporated in the end of the support housing 34A.

An articulation operator 48A on the housing 34A is operably connected to the convex member 44A for rotating the member 44A within the socket 40A so as to articulate the distal end portion 31A (and distal end effector 36A carried thereon) to a desired orientation at an oblique angle relative to the longitudinal axis of the instrument.

An end effector actuator 54A on the housing 34A has an end effector member 52A extending through the convex member passage 50A to actuate the distal end effector 36A.

The embodiments discussed above with reference to FIGS. 1 and 2 incorporate basic forms of the articulable joint assembly of the present invention. Particular, detailed designs of such joint assemblies are described in detail hereinafter as employed in particular instruments.

FIGS. 3-6 illustrate an instrument incorporating an articulable assembly which employs basic design features illustrated in FIG. 1 described above. In particular, the instrument includes an elongate, distal end portion 60 extending from a proximal housing 62.

Figure 5:
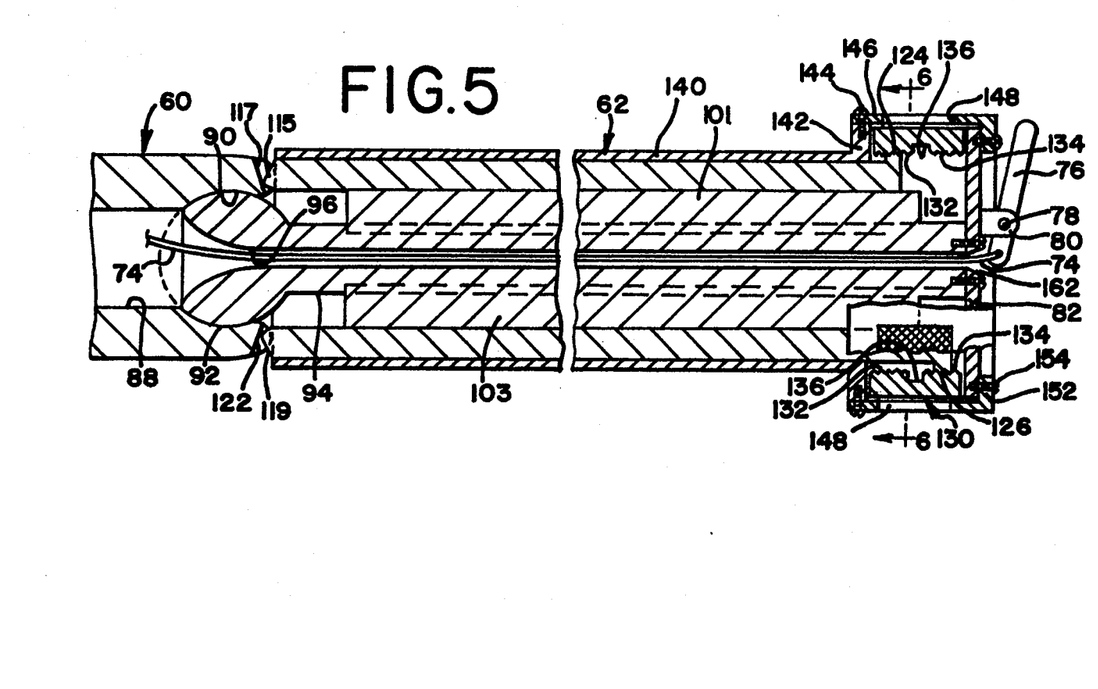
FIG. 5 is an enlarged, fragmentary, cross-sectional view taken generally along the plane 5—5 in FIG. 3.

At the distal end of the portion 60 are a pair of jaws 64 and 66. The jaw 64 is fixed to the end portion 60, but the jaw 66 is pivotally mounted to the end portion 60 with a screw 68 for movement toward and away from the fixed jaw 64. A leaf spring 70 mounted to the end portion 60 normally biases the jaw 66 to an open position. The jaw 66 has a downwardly projecting leg 72 to which is attached a cable 74 extending through the instrument to the proximal end where the cable 74 is attached to a lever 76. As illustrated in FIG. 5, the lever 76 is pivotally mounted on a pin 78 to a clevis 80 projecting from a rear plate 82. The lever 76 can be pivoted forwardly or rearwardly, as illustrated by the double headed arrow 84 in FIG. 3, so as to close the jaw 66 or permit it to be held open by the spring 70.

The elongate, distal end portion 60 defines an interior passage 88, as illustrated in FIGS. 3 and 5, for accommodating the cord or cable 74. As illustrated in FIG. 5, the proximal end of the end portion 60 has an open end defining a concave surface or socket 90. The socket 90 receives a convex member or ball 92 which defines the distal end of an elongate shaft 94. The convex member 92 and shaft 94 define an internal passageway 96 for the cable 74.

Figure 6:
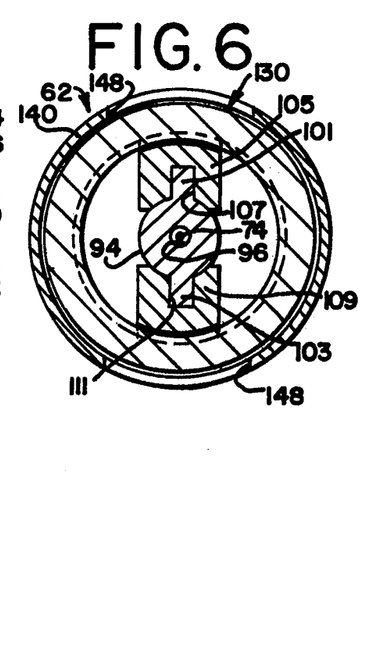
FIG. 6 is a cross-sectional view taken generally along the plane 6—6 in FIG. 5.

As illustrated in FIG. 6, the elongate shaft 94 has two outwardly projecting keys or guide members 101 and 103. A first drive member 105 defines an elongate slot 107 for receiving the guide member 101. A second drive member 109 is diametrically disposed relative to the first drive member 105 and defines a slot 111 for receiving the guide member 103. Each drive member 105 and 109 is thus carried on the elongate shaft 94 for longitudinal movement along the shaft 94 toward and away from the convex member 92.

Figure 4:
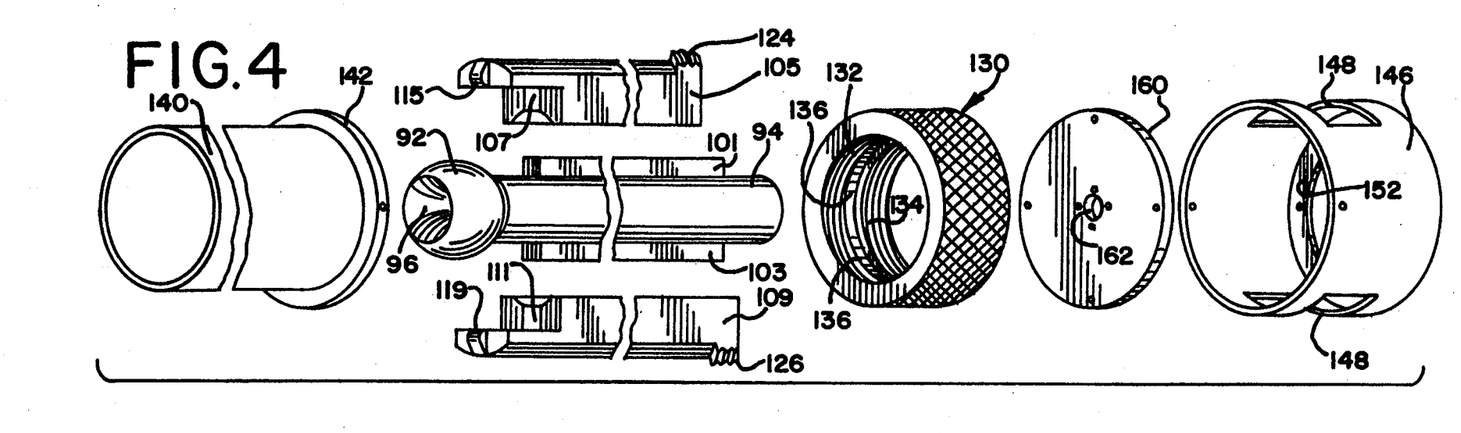
FIG. 4 is an exploded, fragmentary, perspective view of the instrument shown in FIG. 3.

As best illustrated in FIGS. 3-5, the drive member 105 has a distal end defining a tooth 115. The tooth 115 is received in a notch 117 defined in the proximal end of the distal end portion 60.

Similarly, the second drive member 109 has a distal end defining a tooth 119 which is received in a notch 122 defined in the proximal end of the distal end portion 60. In the preferred form illustrated, the distal end portion 60 has a cylindrical exterior configuration, and the notches 117 and 122 are diametrically opposed.

The drive member 105 defines an outwardly oriented left-hand thread segment 124, and the second drive member 109 defines an outwardly oriented right-hand thread segment 126. The thread segments 124 and 126 are threadingly engaged with an articulation operator nut or sleeve 130. The nut or sleeve 130 has a forward cylindrical interior surface which defines a left-hand thread portion 132 and has a rearward cylindrical interior surface which defines a right-hand thread portion 134. The left-hand thread portion 132 is separated from the right-hand thread portion 134 by a cylindrical space 136.

The left-hand thread segment 124 of the first drive member 105 threadingly engages the left-hand thread portion 132 of the sleeve 130, and the right-hand thread segment 126 of the second drive member 109 threadingly engages the right-hand thread portion 134 of the sleeve 130.

When the sleeve 130 is rotated, the engaged left-hand threads 124 and 132 move the first drive member 105 longitudinally (proximally or distally depending upon the direction of rotation of the sleeve 130). At the same time, the drive member 109 is moved in the opposite longitudinal direction owing to the engagement of the right-hand thread segments 126 and 134. As one drive member moves distally, the other drive member moves an equal distance proximally. The distal end of the distally moving drive member forces the instrument distal end portion 60 to pivot about the convex member 92. The pivoting is accommodated by the other drive member moving proximally.

The drive members 105 and 109 are retained within an outer tube 140. The outer tube 140 has a flange 142 at the proximal end which is fastened, as with screws 144, to a retaining ring 146. The retaining ring 146 defines a pair of access apertures 148 which accommodate placement of one or more fingers on the exterior of the sleeve 130 to effect rotation thereof.

The proximal end of the retainer ring 146 has an inwardly projecting, annular flange 152 which is fastened, as with screws 154, to the end plate 82. The end plate 82 defines an aperture 162 for accommodating the cord or cable 74 which is attached to the lever 76. The plate 82 also serves as a base to which the lever clevis 80 is attached.

In operation, the surgeon can hold the exterior of the instrument's outer casing 140 in one hand. With a finger of the other hand, the surgeon can rotate the sleeve 130 as necessary to articulate the distal end portion to the desired orientation. The lever 76 can then be operated to actuate the end effector.

It will be appreciated that the embodiment of the articulable assembly incorporated in the instrument illustrated in FIGS. 3-6 provides a number of advantages. First, the articulation is positively driven through a threaded drive system. Thus, the articulable assembly has no stored energy mechanisms (e.g., springs or members under tension or compression, etc.) for maintaining the articulated position. Therefor, in the event of a component failure, there will not be an uncontrolled movement of the distal end portion of the instrument.

Further, the articulable assembly can be preloaded (without backlash) so as to maintain preload throughout the stroke.

The novel design also accommodates various types of end effector actuator systems. For example, a particular end effector could be provided with a flexible compression member actuator system in place of the tension cable 74. Other types of actuating systems could also be employed and extend through the central passage 96. These could include hydraulic lines, electric lines, and the like. Further, the central passage 96 can accommodate systems other than actuator systems. For example, electrical sensor lines or optical fibers can be routed through the central passage 96. In addition, conduits for supplying fluid to the surgical site, or for withdrawing gas or liquid from the surgical site, could be employed in the central passage 96.

Figure 8:
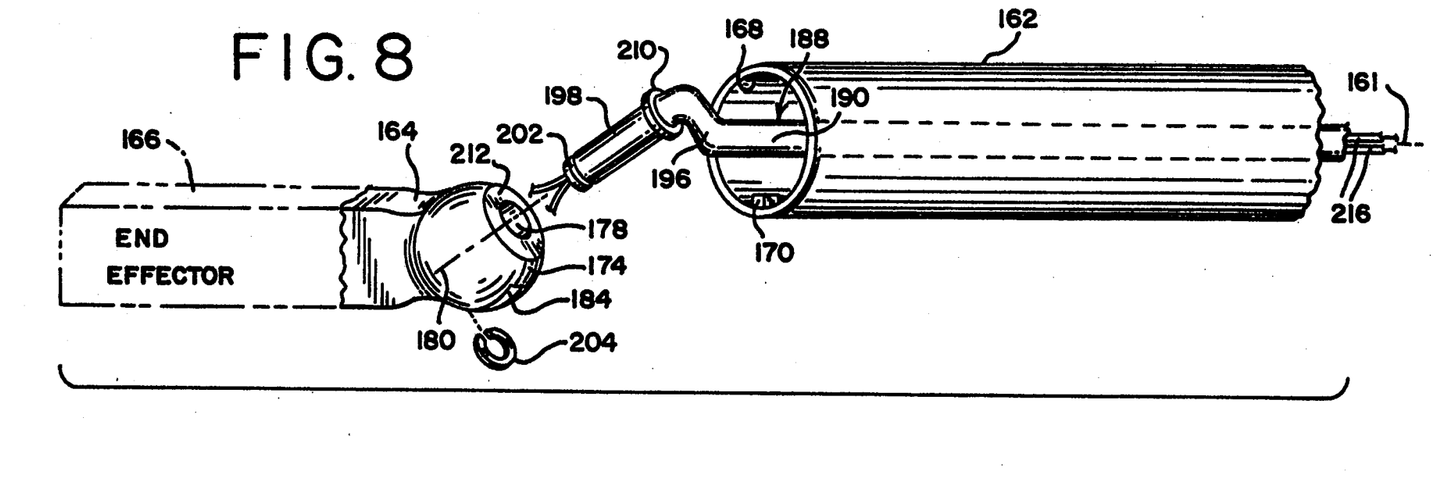
FIG. 8 is an exploded, fragmentary, perspective view of the instrument shown in FIG. 7.
Figure 9:
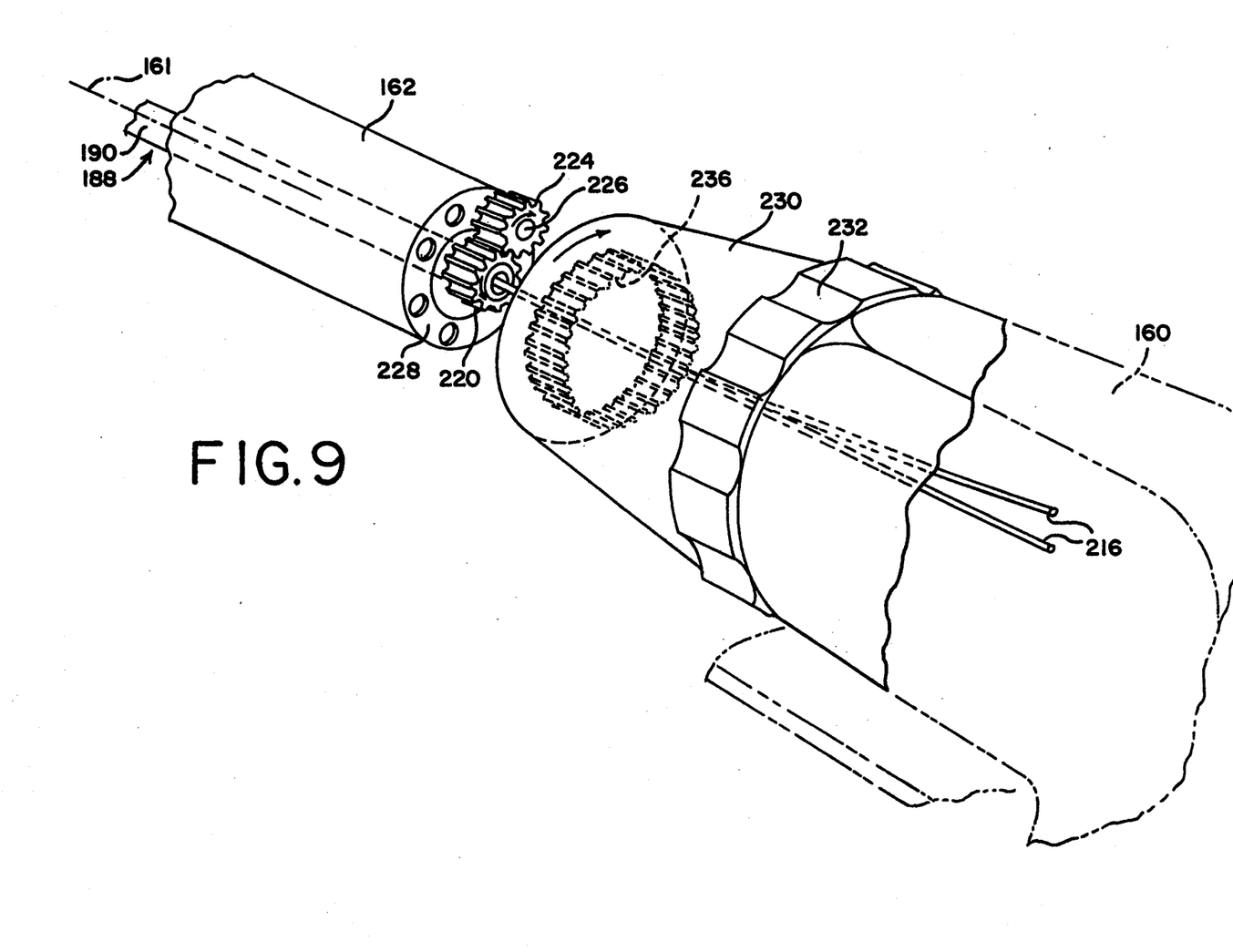
FIG. 9 is a fragmentary, exploded, perspective view of a proximal portion of the instrument shown in FIG. 8.
Figures 10, 11:
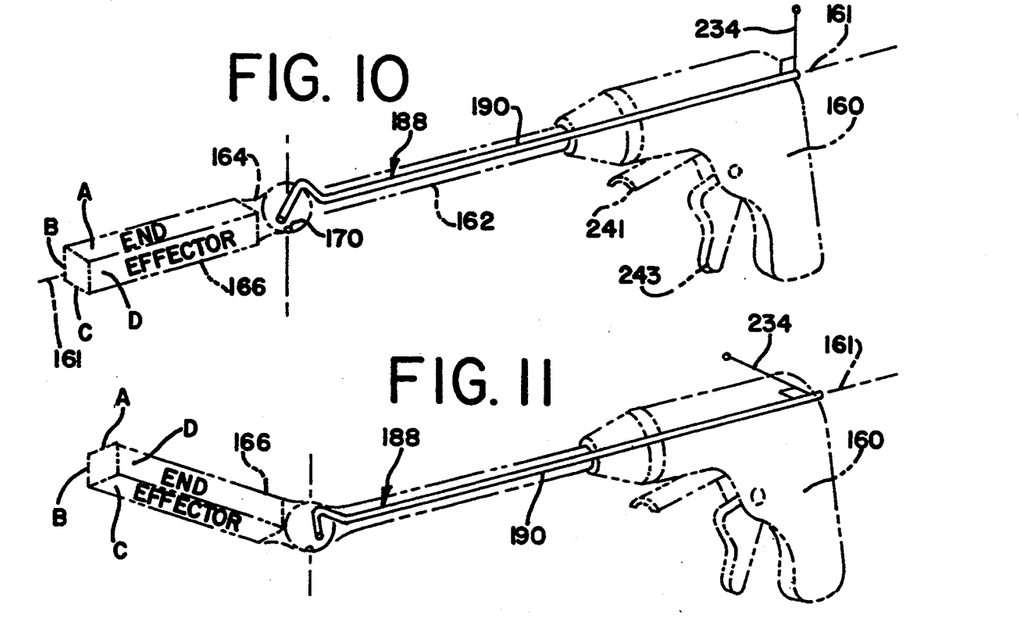
FIGS. 10–13 are simplified, schematic diagrams showing the articulation of the end effector in the instrument illustrated in FIGS. 7-9.

Another embodiment of the articulable assembly of the present invention is illustrated as incorporated in an instrument in FIGS. 7-13. As shown in FIG. 10, the instrument includes a proximal handle portion 160, an elongate housing or support tube 162 which defines a longitudinal axis 161, and a distal end portion 164 for supporting an end effector 166. The end effector 166 may be one of the types discussed above with reference to the instruments illustrated in FIGS. 1-6. The detailed design and operation of the end effector 166 form no part of the present invention.

Figure 7:
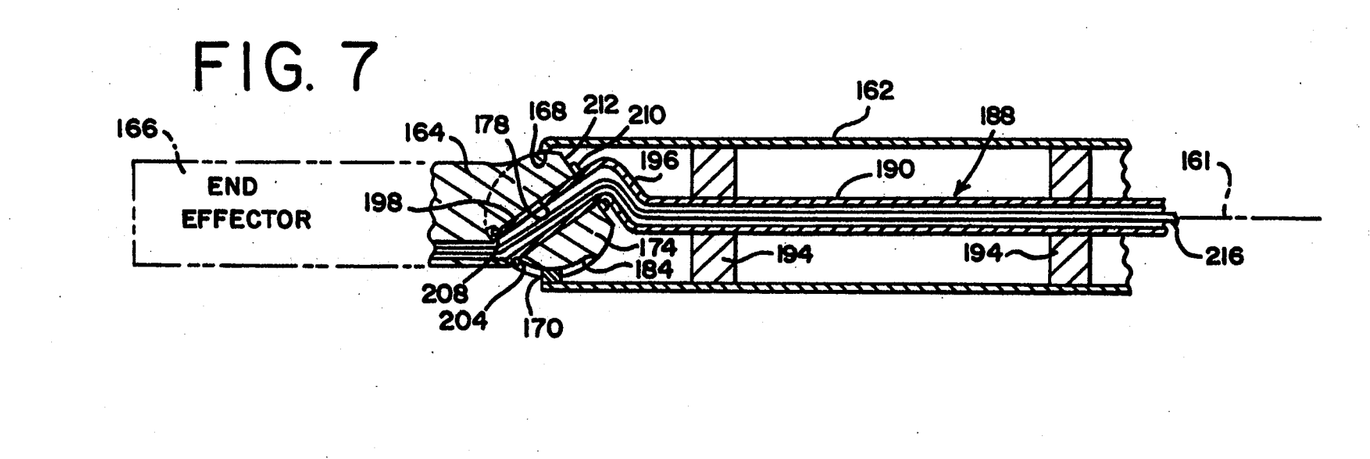
FIG. 7 is a fragmentary, cross-sectional view of a second embodiment of an articulable assembly incorporated in an endoscopic instrument.

The device illustrated in FIGS. 7-13 incorporates the basic invention principles which are schematically illustrated in FIG. 2 described above. In particular, and as illustrated in FIGS. 7 and 8, the housing or support tube 162 has a generally hollow, cylindrical configuration defining a socket 168 at the distal end. A tab 170 projects inwardly from the open end of the tube 162 at the socket region. In the preferred embodiment illustrated, the tab 170 has a rectangular prism shape.

The distal end portion 164 includes a convex member 174 which is received in the socket 168. The convex member 174 defines a passageway 178 oriented with its longitudinal axis 180 (FIG. 8) at an oblique angle relative to the longitudinal axis 161. The convex member 174 also defines an arcuate groove 184 for receiving the tab 170.

An articulation operator is provided on the elongate support tube 162 for moving the distal end portion 164 into and out of alignment with the elongate support tube 162. The articulation operator includes a shaft 188 disposed inside of the support tube 162. The shaft 188 has a proximal portion 190 generally aligned with the longitudinal axis 161. In the embodiment illustrated in FIG. 7, the shaft proximal portion 190 is supported for rotation about the longitudinal axis 161 by two bearings 194 which are mounted within the tube 162.

The shaft 188 also includes an intermediate portion 196 which extends from the proximal portion 190 at an oblique angle relative to the longitudinal axis 161. A distal portion 198 extends from the intermediate portion 196 and is disposed for rotation within the convex member passageway 178.

The distal end of the shaft distal portion 198 defines a groove 202 (FIG. 8) for receiving a snap ring or clip 204. A bottom portion of the convex member 174 defines a clearance or slot 208 (FIG. 7) generally transverse to both the slot 184 and axis 180 for receiving the clip 204. Further, the shaft 188 is provided with a flange 210 (FIG. 7 and FIG. 8) on the distal portion 198. Thus, the distal portion 198 can be inserted into the convex member passageway 178 until the flange 210 abuts a generally planar, annular, bearing surface 212 at one end of the convex member 174. The clip 204 can then be inserted through the convex member slot 208 to engage the shaft distal portion 198 in the groove 202. This holds the convex member 174 on the shaft distal portion 198. However, the shaft distal portion 198 is free to rotate about the axis 180 (FIG. 8) within the convex member passageway 178.

The shaft 188 is hollow and accommodates one or more end effector actuator components, such as cables 216, and can also accommodate sensor components (not illustrated), fluid transfer tubing (not illustrated), and the like. Such components are generally flexible to accommodate rotation of the shaft 188 and concomitant articulation of the end effector 166 as explained in detail hereinafter.

In a preferred embodiment, the shaft proximal portion 190 can be rotated about the longitudinal axis 161 by a gear drive system as illustrated in FIG. 9. In particular, a central gear 220 is mounted to the shaft proximal portion 190 so that rotation of the gear 220 would effect rotation of the proximal portion 190 about the axis 161. A gear 224 is mounted for rotation on a mounting pin 226 projecting from a flange 228 at the proximal end of the support tube 162. The gear 224 meshes with the gear 220.

The housing 160 includes a rotatable, frustoconical, drive sleeve 230 with an exterior bezel surface 232 which can be grasped between the surgeon's thumb and forefinger to rotate the sleeve 230. The distal end of the sleeve 230 includes an interior, cylindrical surface for engaging a portion of the exterior surface of the support tube 162. Further, recessed inwardly in the sleeve 230 is a ring gear 236 for engaging the gear 224. Rotation of the sleeve 230 thus effects rotation of the gears 236, 224, and 220 to rotate the shaft 188.

When the shaft 188 rotates, the orientation of the end effector 166 is changed as illustrated in FIGS. 10-13. It will be appreciated that the tab 170 (FIG. 7) engages the side walls of the slot 184 in the convex member 174. This functions as a fixed pivot point while the convex member 174, and hence slot 184, are moved together within the socket 168 by the offset distal end portion 178 of the shaft 188.

In FIGS. 10-13, an operating handle or lever 234 is schematically represented as being connected to the proximal end of the shaft 188. Such an operating handle 234 can be used in lieu of a drive sleeve 230 and gear drive system illustrated in FIG. 9.

The handle 234 is illustrated in FIGS. 10-13 primarily for the purpose of conveniently showing the rotational position of the shaft 188 relative to the articulated orientation of the end effector 166. The handle 234 is fixed at a right angle to the proximal portion 190 of the shaft 188, and therefore the relationship between the rotation of the shaft 188 and the movement of the end effector 166 can be more readily observed in FIGS. 10-13.

The end effector 166 is schematically represented as a rectangular parallelpiped having four, side surfaces A, B, C, and D. This permits the orientation of the end effector to be more easily understood in the two-dimensional illustrations which constitute FIGS. 10-13.

In particular, FIG. 10 illustrates the end effector 166 oriented substantially in alignment along the longitudinal axis 161 of the instrument. The end effector 166 is viewed at an angle from the front and from above. Surface A faces upwardly, and surface C faces downwardly. In this position the handle 234 projects vertically upwardly at a 90° angle relative to the proximal portion 190 of the shaft 188.

When the handle is rotated 90° counter-clockwise as viewed in FIG. 11 so as to rotate the shaft proximal portion 190 counterclockwise 90°, the end effector 166 swings toward the viewer and upwardly. Surface C is now visible to the viewer along with surface D.

Figure 12:
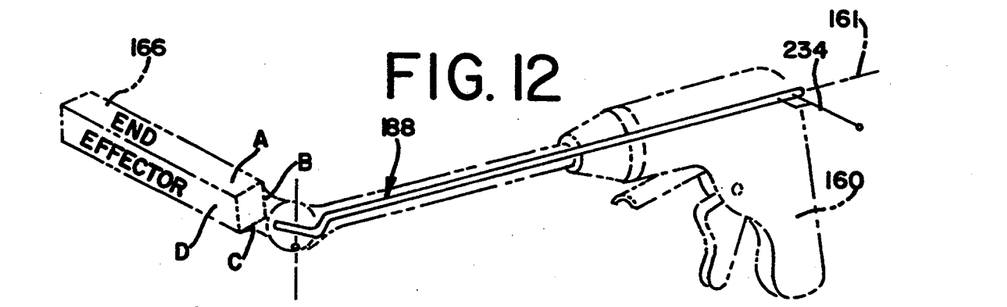

When the handle 234 is pivoted 90° clockwise as viewed in FIG. 12, the end effector 166 swings away from the viewer and upwardly in a generally opposite, mirror-image relationship to that shown in FIG. 11. Surface A is now visible to the viewer along with surface D.

Figure 13:
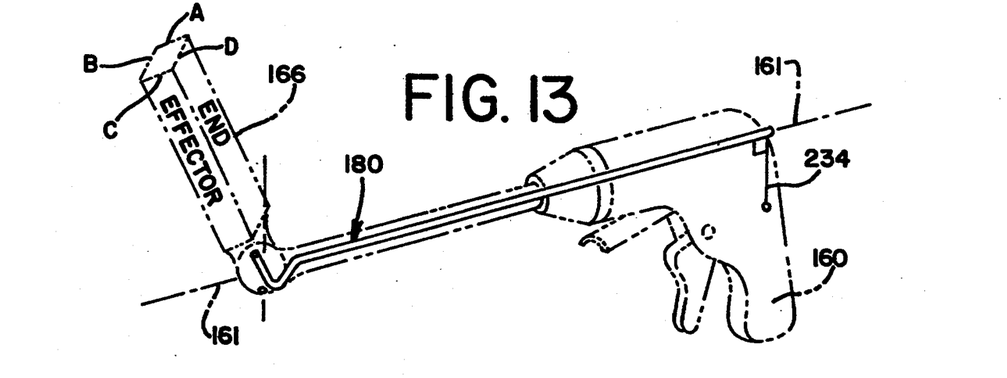

When the handle 234 is pivoted 180° from the position illustrated in FIG. 10 to the position illustrated in FIG. 13, the distal end of the end effector 166 becomes offset above the longitudinal axis 161 by a maximum amount, and the end effector 166 lies midway between the two lateral positions of the end effector in FIGS. 11 and 12. Surfaces C and D are now visible.

The instrument handle portion 160 can include suitable triggers 241 and 243 (FIG. 10) for actuating the end effector flexible actuating components (e.g., flexible cables, hydraulic systems, etc.) or other devices, systems, or components.

Although not illustrated, the elongate support tube 162 may also include appropriate gas seals, filters, or venting systems. Further, in some applications, it may be desirable to line the socket 168 with a low-friction, bearing material, such as a suitable thermoplastic polymer.

Figures 14, 17:
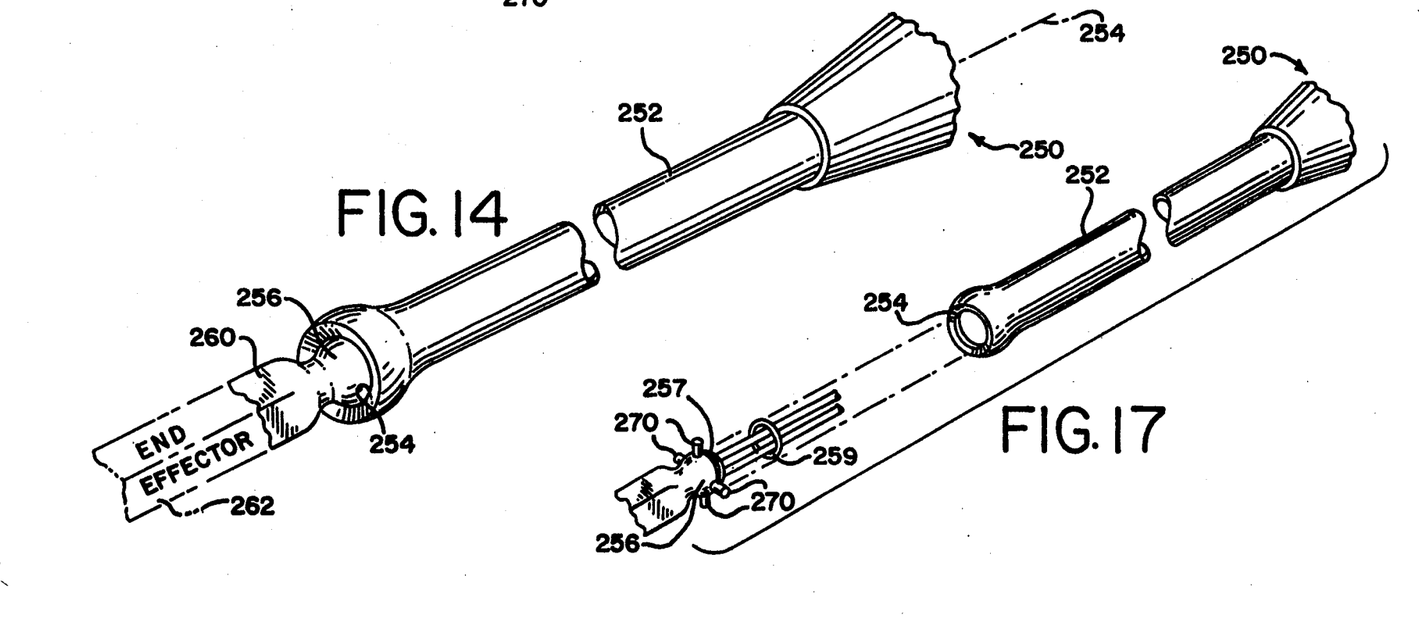
FIG. 14 is a fragmentary, perspective view of a third embodiment of an articulable assembly for an endoscopic instrument.
FIG. 17 is an exploded, fragmentary, perspective view of the instrument shown in FIGS. 14-16.
Figure 15:
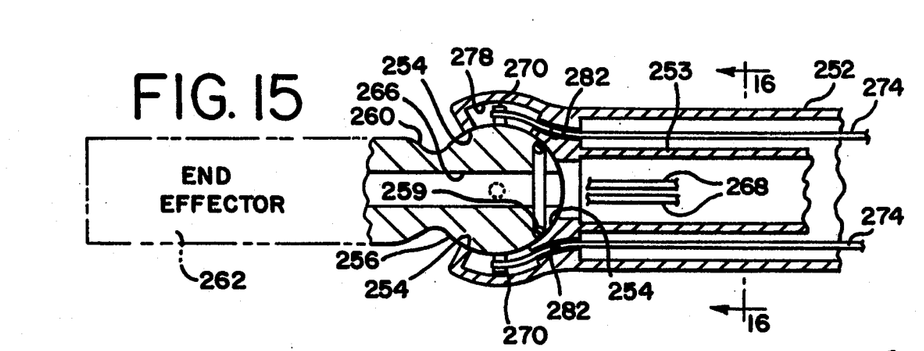
FIG. 15 is an enlarged, fragmentary, cross-sectional view of the instrument shown in FIG. 14.
Figures 18, 19, 20:
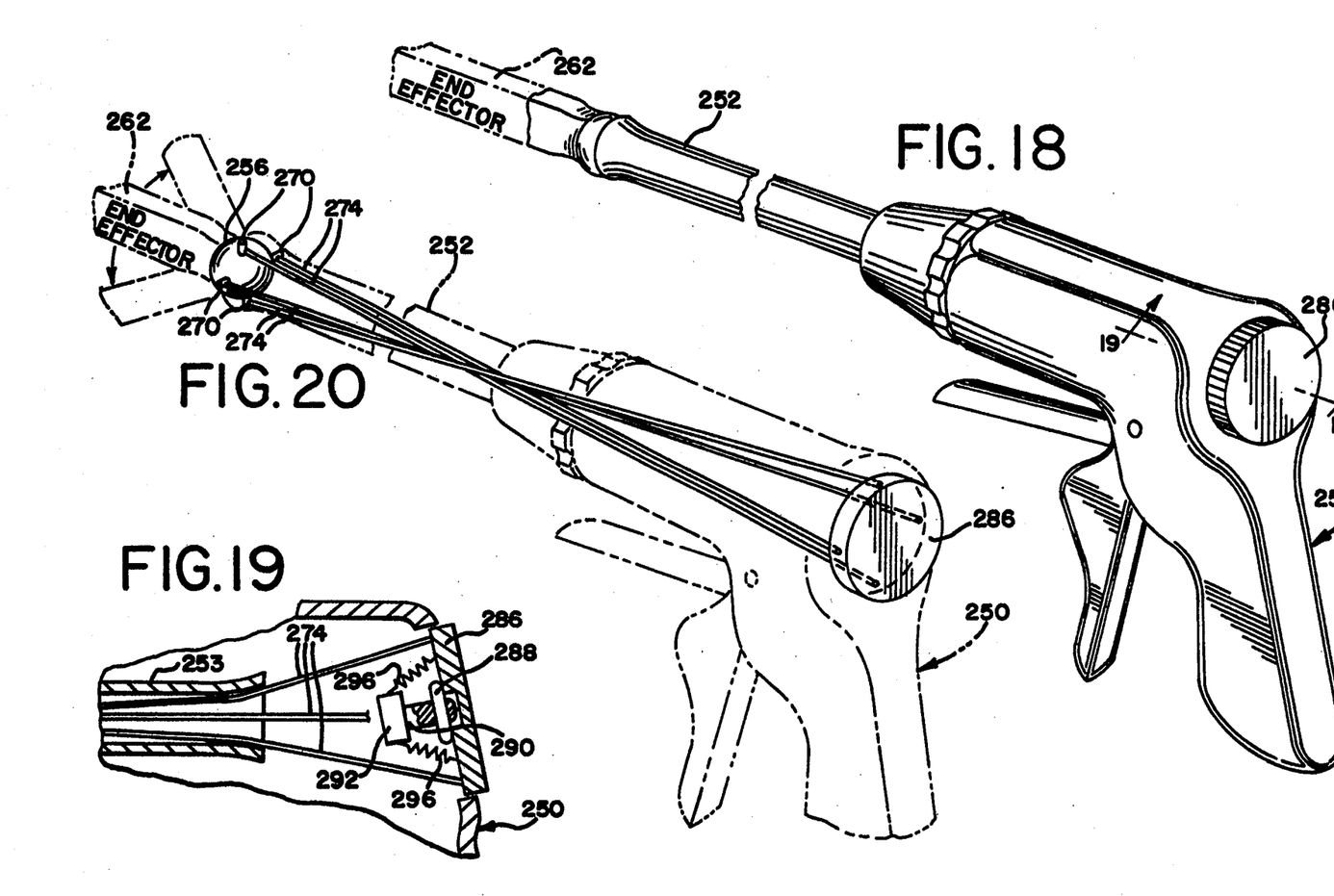
FIG. 18 is a rear, perspective view of the instrument shown in FIGS. 14-17.
FIG. 19 is an enlarged, fragmentary, cross-sectional view taken generally along the plane 19—19 in FIG. 18.
FIG. 20 is a view similar to FIG. 18, but showing portions of the instrument in phantom with dashed lines to reveal interior detail.

Another embodiment of the articulable assembly of the present invention is incorporated in an instrument as illustrated in FIGS. 14-20. The embodiment illustrated in FIGS. 14-20 employs the principles of the invention in the form as schematically illustrated in FIG. 2. In particular, as illustrated in FIG. 18, the instrument includes a proximal portion 250 from which extends a hollow support tube or housing 252 defining a longitudinal axis 254 (FIG. 14). The support tube or housing 252 includes an internal tube 253 as best illustrated in FIGS. 15 and 19. As illustrated in FIG. 17, the support tube 252 has an enlarged end defining an open socket 254 for receiving a convex member 256 which defines the proximal part of a distal end portion 260 of the instrument. The distal end portion 260 supports an end effector 262. The end effector 262 may be one of the various end effectors discussed above with reference to FIGS. 1-6.

Preferably, as illustrated in FIGS. 15 and 17, the convex member 256 defines an annular groove 257 for receiving an o-ring 259 for effecting a seal of the joint assembly within the instrument.

The convex member 256 also defines a passage 266 for accommodating internal components such as an actuator member, hydraulic line, sensor line, etc. Two flexible lines 268 are illustrated in FIGS. 15 and 16 as extending through the instrument.

As illustrated in FIGS. 15, 17, and 20, the convex member 256 includes four, equally spaced-apart, radially extending projections 270. A cable or cord 274 is looped around or otherwise fastened to each projection 270. Each projection 270 and the fastened end of the associated cord 274 are received in a circumferencial channel or recess 278 in the enlarged end of the support tube 252.

Figure 16:
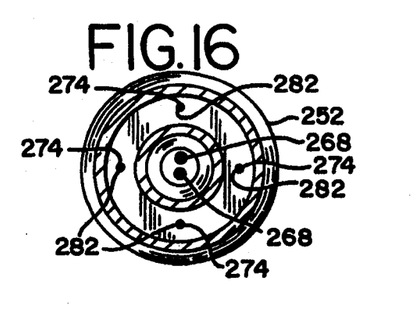
FIG. 16 is a cross-sectional view taken generally along the plane 16—16 in FIG. 15.

As illustrated in FIGS. 15 and 16, the internal portion of the tube 252 adjacent the socket 254 defines four apertures 282 for each receiving one of the cords 274. The cords 274 extend along the inside of the support tube 252 and, as illustrated in FIG. 20, cross and diverge to opposite positions relative to the longitudinal axis of the support tube 252.

As illustrated in FIG. 20, the proximal end of each cord 274 is fastened to a wobble plate 286. As shown in FIG. 19, the plate 286 is held against a flange 288 on a post 290 projecting from a bracket 292 carried on the inside of the instrument proximal portion 250. Extending between the plate 286 and the bracket 292 are four tension springs 296 (only two of which are shown in FIG. 19). These hold the plate 286 against the flange 288.

When the instrument proximal portion 250 is held in one hand, a selected peripheral region of the plate 286 can be pushed inwardly with a thumb. This causes one or more of the springs 296 to contract while one or more of the other springs 296 are extended. The tilting of the plate 286 from the normal, rest position illustrated in FIG. 19 results in one or more of the cords 274 being pulled rearwardly (proximally) while one or more of the other cords 274 are relaxed. This causes a rotation or swiveling of the convex member 256 in the socket 254. This results in articulation of the end effector 262. Because the cords 274 cross in opposite directions as illustrated in FIG. 20, pushing on one quadrant region of the plate 286 will cause the end effector 262 to articulate generally in the direction toward which that quadrant region of the plate 286 is pushed.

The support tube 252 may include additional seals, vents, filters, etc. (not illustrated). Further, various actuating mechanisms, end effector devices, sensor lines, electric power lines, and the like, may be provided within the tube 253 and may extend through the joint assembly passage 266.

Figures 21, 22:
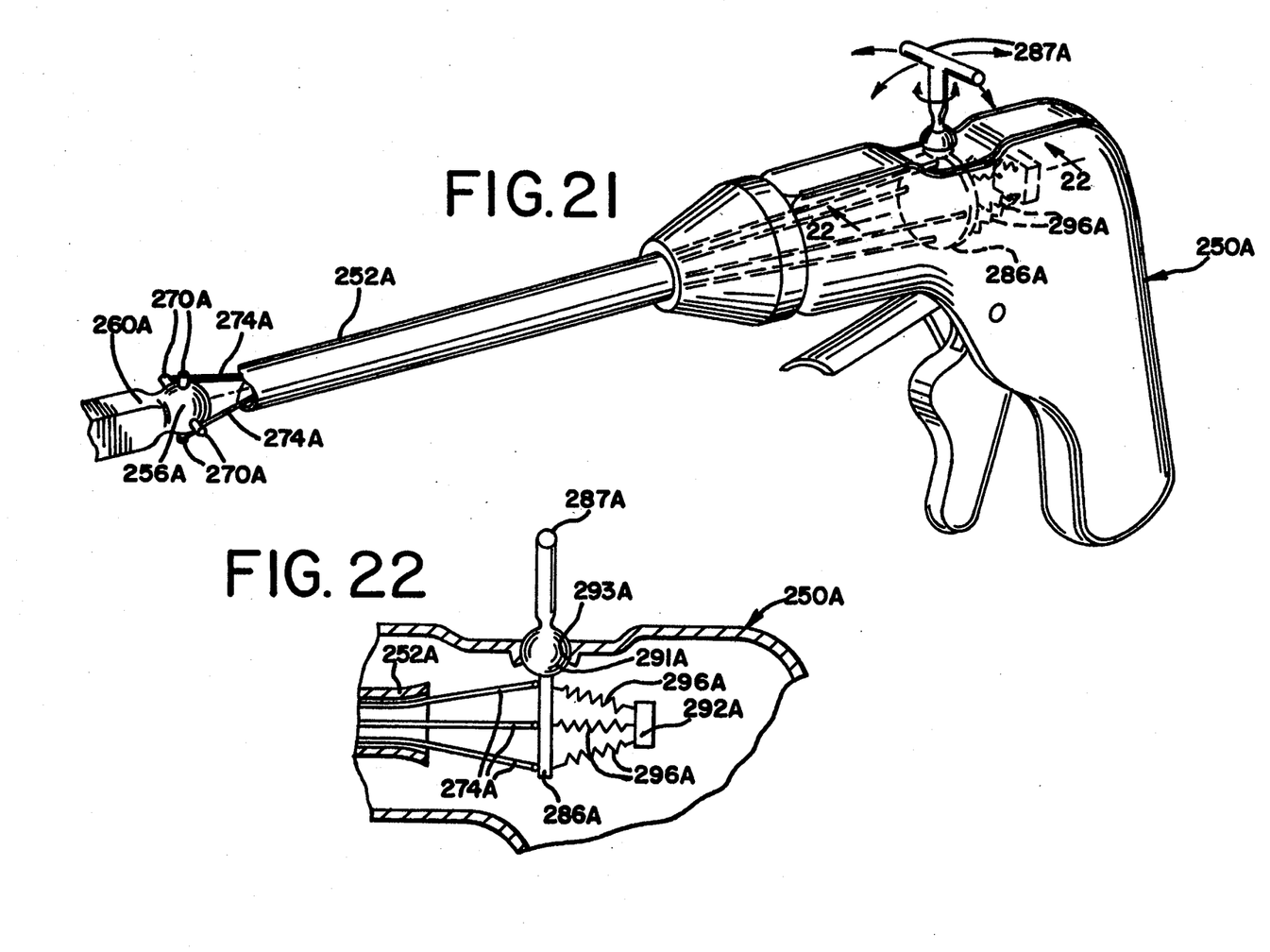
FIG. 21 is a fragmentary, perspective view of a modified form of the instrument illustrated in FIGS. 14-20.
FIG. 22 is an enlarged, fragmentary, cross-sectional view taken generally along the plane 22—22 in FIG. 21.

A modification of the instrument illustrated in FIGS. 14-20 is shown in FIGS. 21 and 22. The instrument includes an elongate support tube or housing 252A for supporting a distal end portion 260A extending from a convex member 256A. Cords or cables 274A extend from projections 270A on the convex member through the tube 252A to a proximal portion 250A of the instrument. The components so far described are substantially identical to those components having the same numbers without the "A" identified above with reference to the embodiment illustrated in FIGS. 14-20. However, in this modified form illustrated in FIGS. 21 and 22, the instrument does not have an actuator plate 286 mounted at the proximal end as shown in FIG. 18. Rather, an actuator plate 286A is mounted within a proximal portion 250A of the instrument, and a T-shaped operating lever 287A extends upwardly through the top of the instrument. The handle 287A includes a spherical base 291A received in an arcuate socket 293A. The cables 274A are attached at four, equally spaced locations around the front of the plate 286A. The rear side of the plate 286A is connected at corresponding locations to tension springs 296A. The proximal ends of the springs 296A are attached to a bracket 292A mounted on the inside of the instrument proximal portion 250A.

The four springs 296A normally maintain the plate 286A in a neutral position as illustrated in FIG. 22 with equal tension on each of the cords 274A. When the handle 287A is moved from the position illustrated in FIGS. 21 and 22, some of the cords 274A are pulled while others are relaxed so as to effect swiveling of the convex member 256A and articulation of the distal end portion 260A.

FIGS. 23–29 illustrate another aspect of this invention which provides a track for guiding surgical fasteners, such as staples or clips, through an articulable joint. In particular, an articulable joint assembly similar to the one described above with reference to FIGS. 14–20 can be employed in an instrument for feeding and applying ligating clips to tissue, such as a blood vessel.

Figures 23, 24, 25, 26, 27, 28, 29:
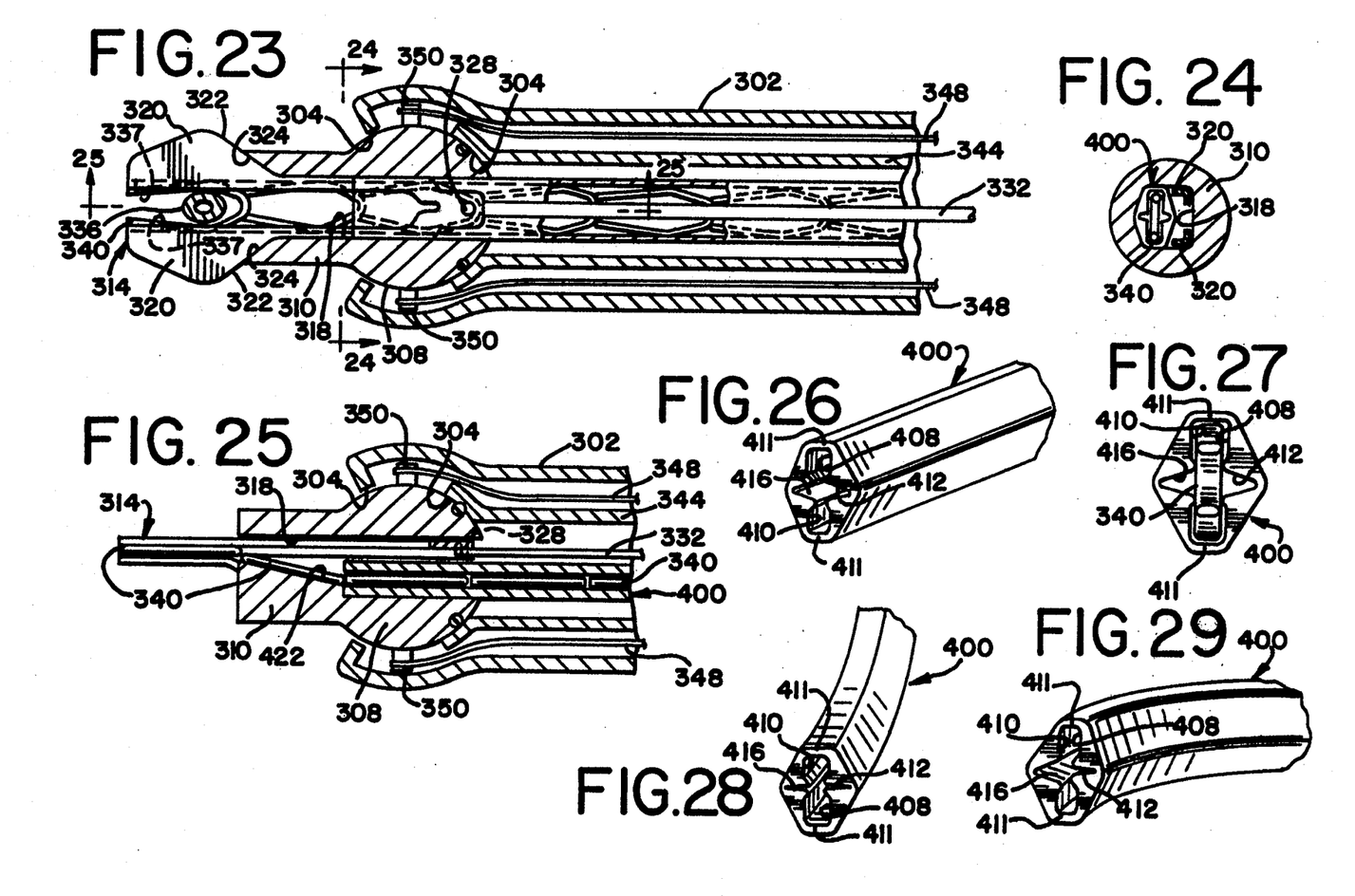
FIG. 23 is a fragmentary, cross-sectional view of a fourth embodiment of an articulable assembly of the present invention incorporated in an instrument with a track for guiding a ligating clip in accordance with another aspect of the present invention.
FIG. 24 is a cross-sectional view taken generally along the plane 24—24 in FIG. 23.
FIG. 25 is a fragmentary, cross-sectional view taken generally along the plane 25—25 in FIG. 23.
FIG. 26 is a fragmentary, perspective view of the ligating clip track employed in the instrument illustrated in FIGS. 23-25.
FIG. 27 is a front, end view of the track shown in FIG. 26.
FIG. 28 is a fragmentary, perspective view of the track bending in one plane.
FIG. 29 is a fragmentary, perspective view of the track bending in another plane.

FIGS. 23–25 illustrate a portion of an instrument having an elongate support tube or housing 302 defining a socket 304 in which is mounted a convex member 308. The convex member 308 is defined on a distal end portion 310 which carries an end effector in the form of a jaw assembly 314.

The convex member 308 and distal end portion 310 define a passageway at 318 (FIG. 25) in which the jaw assembly 314 is mounted. The jaw assembly 314 has a generally U-shaped configuration with the legs of the "U" each defining a jaw 320. Each jaw 320 has a rearwardly facing cam surface 322 for engaging a slanted surface 324 at the distal end of the end portion 310 (FIG. 23). The jaw assembly 314 is connected at its proximal end with a pin 328 to a flexible member or cable 332. The cable 332 can be pulled rearwardly by suitable means (not illustrated). This causes the jaw assembly 314 to be moved further into the instrument which causes the jaws to be cammed together to close about tissue, such as a blood vessel 336 (FIG. 23).

Each jaw 320 also defines a channel 337 (FIG. 23) for receiving a generally U-shaped ligating clip 340 which can be positioned in the distal portion of the jaws 320 (as described in detail hereinafter). When the jaws 320 are closed, the clip 314 is squeezed and crimped about the tissue 336.

The elongate support tube 302 has an inner tube 344 extending from the socket 304 around the jaw actuating cable 332. The space between the elongate support tube 302 and the inner tube 344 defines a region for accommodating articulation operator cables 348 which are fastened to projections 350 extending radially outwardly from the surface of the convex member 308. In a preferred embodiment, there are four such projections 350 and four attached cables 348 in substantially the same configuration as described above with respect to the embodiment illustrated in FIGS. 14–20 wherein the convex member 256 has four projections 270 which are each attached to one of the cables 274.

Pulling on one or more of the cables 348 while relaxing one or more of the other cables 348 results in the convex member 308 being swiveled within the socket 304, and this articulates the distal end portion 310. The cables 348 may be tensioned and relaxed by a suitable operating mechanism, such as the wobble plate 286 described above with reference to the embodiment illustrated in FIGS. 14–20.

In accordance with the teachings of one aspect of the present invention, the ligating clips 340 are guided through the articulable joint assembly in a unique track. The track includes a tube 400. The tube 400 is made from material which is sufficiently flexible to accommodate bending through the joint. It is presently contemplated that the tube 400 would be extruded from a suitable elastomeric or thermoplastic material.

The tube 400 defines a longitudinal passage for the ligating clips 340. The passage has a transverse cross sectional configuration for accommodating and maintaining each clip 340 generally in a predetermined orientation while moving along the passage. The clips 340 can be pushed in a line through the tube 400 by a suitable flexible pusher bar (not illustrated) in the proximal portion of the instrument. The design and operation of mechanisms for advancing the clips 340 through the tube 400 form no part of the present invention.

As illustrated in FIG. 27, the passage is at least in part defined by two, generally opposed wall portions 408 and 410. The opposed wall portions 408 and 410 are joined by thin, connecting portions 411. The wall portion 408 defines a longitudinal groove 412, and the wall portion 410 defines a longitudinal groove 416. The grooves 412 and 416 open toward each other, and each groove has a generally V-shape.

As illustrated in FIG. 29, when the track tube 400 is deformed or bent to the right, the opening of the groove 412 decreases while the opening of the groove 416 can increase somewhat. On the other hand, when the track tube 400 is bent or flexed in the opposite direction (not illustrated), the groove 412 would open while the groove 416 would tend to close.

If the track tube 400 is flexed or bent as illustrated in FIG. 28, 90° to the orientation of the bending illustrated in FIG. 29, then both grooves 412 and 416 tend to close or flatten.

The track tube 400 is disposed within the instrument so that the distal end of the tube 400 terminates within the convex member 308 so as to discharge the ligating clips 340 into the passage 318 (FIG. 25). As illustrated in FIG. 25, a portion of the passage 318 is defined by an upwardly slanting ramp surface 422. This surface 422 guides the clips 340 from the end of the track tube 400 into the receiving channels 337 within the jaws 320. When the instrument end portion 310 is articulated, the distal end of track tube 400 will move with the convex member 308, and the tube 400 will bend at a point proximally (rearwardly) of the convex member 308 to accommodate the movement of the member 308.

Although FIGS. 23–25 illustrate only the jaw assembly 314 and track tube 400 in the passage 318, it will be appreciated that modifications can be made to accommodate additional components if desired. Such additional components can include sensor lines, aspirator or suction lines, optical fibers, etc.

It will also be appreciated that the track tube 400 may be employed for guiding fasteners, such as ligating clips or staples, through other types of articulable joints in endoscopic instruments. The track tube 400 is especially suitable for use in guiding fasteners where the tube is subjected to compressive or tensile bending loads that effect the bending of the tube.

It will be readily apparent from the foregoing detailed description of the invention and from the illustrations thereof that numerous other variations and modifications may be effected without departing from the true spirit and scope of the novel concepts or principles of this invention.

What is claimed is:

1. An articulable assembly for an instrument used in an endoscopic procedure, said assembly comprising:
   a distal end portion for supporting an end effector to effect tissue manipulation while carrying out a surgical procedure within a body cavity, said distal end portion having an open end defining a socket;
   an elongate shaft defining a longitudinal passage and terminating in a convex member received in said socket, said convex member having a partially spherical configuration and defining a passageway communicating with said shaft passage for accommodating an actuator extending from said housing to actuate said end effector; and
   an operator on said shaft for moving said distal end portion into and out of alignment with said elongate shaft, said operator including pair of first and second drive members disposed on said shaft for longitudinal movement along said shaft toward and away from said convex member, each said drive member having a distal end engaged with said distal end portion, said first and second drive members defining outwardly oriented left-hand thread segments and right-hand thread segments, respectively, said operator including a sleeve mounted on said drive members for rotation about said shaft, said sleeve having an interior surface defining a left-hand thread portion and a right-hand thread portion for operatively engaging said drive member left-hand thread segments and right-hand thread segments, respectively.

2. An articulable assembly for an instrument used in an endoscopic procedure, said assembly comprising:
   an elongate support tube defining a longitudinal axis and having an open end defining a socket with an inwardly projecting tab;
   a distal end portion connected to said tube for supporting an end effector to effect tissue manipulation while carrying out a surgical procedure within a body cavity, said distal end portion having a convex member received in said socket, said convex member defining a passageway oriented with its axis at an oblique angle relative to said tube longitudinal axis and defining an arcuate groove receiving said tab; and
   an operator on said elongate support tube for moving said distal end portion into and out of alignment with said elongate support tube, said operator including a shaft having (1) a proximal portion in said tube generally aligned with said longitudinal axis, (2) an intermediate portion in said tube extending from said proximal portion at an oblique angle relative to said longitudinal axis, and (3) a distal portion extending from said intermediate portion into said convex member passageway and disposed for rotation in said passageway, said shaft portions being hollow for accommodating an actuator extending from said support tube through said shaft to actuate said end effector.

3. The assembly in accordance with claim 2 in which said convex member passageway is a cylindrical bore and in which said shaft distal portion is cylindrical.

4. An articulable assembly for an instrument used in an endoscopic procedure, said assembly comprising:
   a distal end portion for supporting an end effector to effect tissue manipulation while carrying out a surgical procedure within a body cavity;
   an elongate support housing and an articulable joint connecting said housing with said distal end portion, said joint including a hollow socket and a convex member that is received in said socket and that defines a passageway for accommodating an actuator extending from said housing through said joint to actuate said end effector;
   an operator on said housing and extending to one of said socket and convex member for moving said distal end portion into and out of alignment with said housing;
   said housing including a tube defining a longitudinal axis and having an open end defining said socket with an inwardly projecting tab;
   said distal end portion defining said convex member;
   said convex member defining a passageway oriented with its axis at an oblique angle relative to said tube longitudinal axis and defines an arcuate groove receiving said tab; and
   said operator including a shaft having (1) a proximal portion aligned along said housing tube longitudinal axis, (2) an intermediate portion extending from said proximal portion at an oblique angle relative to said housing tube longitudinal axis, and (3) a distal portion extending from said intermediate portion into said convex member passageway and disposed for rotation in said passageway.

5. The assembly in accordance with claim 4 in which said housing has a proximal end including a handle portion.

6. The assembly in accordance with claim 4 in which said convex member has a convex surface portion; and said socket is defined by the open end of a tube in which said convex surface portion is disposed.

7. An articulable assembly for an instrument used in an endoscopic procedure, said assembly comprising:
   a distal end portion for supporting an end effector to effect tissue manipulation while carrying out a surgical procedure within a body cavity;
   an elongate support housing and an articulable joint connecting said housing with said distal end portion, said joint including a hollow socket and a convex member that is received in said socket and that defines a passageway for accommodating an actuator extending from said housing through said joint to actuate said end effector;
   an operator on said housing and extending to one of said socket and convex member for moving said distal end portion into and out of alignment with said housing;
   said distal end portion including a tube having an open end defining said socket;
   said housing including a shaft to which said convex member is attached and which defines a longitudinal passage;
   said convex member having a partially spherical configuration in which said passageway is defined as a central aperture communicating with said shaft passage;
   said operator including a pair of first and second drive members diametrically disposed on said shaft for longitudinal movement along said shaft toward and away from said convex member, each said drive member having a distal end engaged with said open end of said heat tube, said first and second drive members defining outwardly oriented left-hand thread segments and right-hand thread segments, respectively; and said operator including a sleeve mounted on said drive members for rotation about said shaft, said sleeve having an interior surface defining a left-hand thread portion and a right-hand thread portion for engaging said drive member left-hand thread segments and right-hand thread segments, respectively.

8. The assembly of claim 1 further including a joint connecting said distal end portion and said shaft containing a tube of material sufficiently flexible to accommodate bending through said joint, said tube defining a longitudinal passage with a transverse cross sectional configuration for accommodating and maintaining said fastener generally in a predetermined orientation while moving along said passage, said tube passage being at least in part defined by two, generally opposed wall portions, each said wall portion defining a longitudinal groove that is open toward the other of said wall portions whereby the groove opening can vary in response to compressive and tensile bending loads.

9. The track in accordance with claim 8 in which each said groove has a generally V-shaped configuration when said tube is unstressed.

10. The track in accordance with claim 8 in which said passage has a width dimension and a height dimension which is less than the width dimension.

11. The track in accordance with claim 8 in which said tube includes two, opposed, connecting portions connecting said two, opposed wall portions.

* * * * *